(12) United States Patent
Bacon

(10) Patent No.: US 9,415,178 B2
(45) Date of Patent: Aug. 16, 2016

(54) COUNTER

(75) Inventor: Raymond Bacon, Petersfield (GB)

(73) Assignee: EURO-CELTIQUE S.A., Luxemburg (LU)

(*) Notice: Subject to any disclaimer, the term of this patent is extended or adjusted under 35 U.S.C. 154(b) by 1271 days.

(21) Appl. No.: 13/138,604

(22) PCT Filed: Mar. 10, 2010

(86) PCT No.: PCT/GB2010/050405
§ 371 (c)(1),
(2), (4) Date: Oct. 17, 2011

(87) PCT Pub. No.: WO2010/103316
PCT Pub. Date: Sep. 16, 2010

(65) Prior Publication Data
US 2012/0017900 A1    Jan. 26, 2012

(30) Foreign Application Priority Data
Mar. 10, 2009  (GB) .................................. 0904059.3

(51) Int. Cl.
*A61M 15/00* (2006.01)
*G06M 1/00* (2006.01)
(Continued)

(52) U.S. Cl.
CPC .......... *A61M 15/009* (2013.01); *A61M 15/0065* (2013.01); *A61M 15/0078* (2014.02); *G06M 1/163* (2013.01); *G06M 1/245* (2013.01); *G06M 1/248* (2013.01)

(58) Field of Classification Search
CPC .......... A61M 15/0068; A61M 15/007; A61M 15/0071; A61M 15/0075; A61M 15/0076; A61M 15/0078; A61M 15/009; A61M 15/0065; G06M 1/22–1/26; G06M 1/00; G06M 1/04; G06M 1/041; G06M 1/08; G06M 1/083; G06M 1/16; G06M 1/163
See application file for complete search history.

(56) References Cited

U.S. PATENT DOCUMENTS 2,002,835 A   5/1935 Rose
2,716,013 A   8/1955 Tinker
(Continued)

FOREIGN PATENT DOCUMENTS

AU      776816      7/2002
AU   2003234746    9/2003
(Continued)

OTHER PUBLICATIONS

International Search Report for PCT/GB2010/050405, mailed Jun. 16, 2010.
(Continued)

*Primary Examiner* — Justine Yu
*Assistant Examiner* — Timothy Stanis
(74) *Attorney, Agent, or Firm* — Nixon & Vanderhye P.C.

(57) ABSTRACT

The present invention provices a counter comprising: a first member disposed in at least a partial helical turn about a longitudinal axis of an entity whose movements and/or contents are to be counted, said first member having an indicium or indicia indicative of a count; a second member extending generally in the direction of said longitudinal axis, said second member being operatively disposed in overlapping relationship under and over one or more portions of said at least partial helical turn of said first member; and means to effect relative movement between said first and second members, said movement comprising a relative incremental rotation about said longitudinal axis.

31 Claims, 5 Drawing Sheets

(51) Int. Cl.
  *G06M 1/16* (2006.01)
  *G06M 1/24* (2006.01)

(56) References Cited

U.S. PATENT DOCUMENTS

| | | |
|---|---|---|
| 2,922,613 A | 6/1960 | Beecham |
| 3,103,335 A | 9/1963 | Martinez |
| 3,190,497 A | 6/1965 | Anthon |
| 3,329,389 A | 7/1967 | Clark |
| 3,598,288 A | 8/1971 | Posgate |
| 3,746,196 A | 7/1973 | Sako |
| 4,142,651 A | 3/1979 | Leopoldi |
| 4,361,148 A | 11/1982 | Shackleford |
| 4,370,368 A | 1/1983 | Hirata |
| 4,393,106 A | 7/1983 | Maruhashi |
| 4,486,378 A | 12/1984 | Hirata |
| 4,576,157 A | 3/1986 | Raghuprasad |
| 4,664,107 A | 5/1987 | Wass |
| 4,753,371 A | 6/1988 | Michielin |
| 4,817,822 A | 4/1989 | Rand |
| 4,955,371 A | 9/1990 | Zamba |
| 4,984,158 A | 1/1991 | Hillsman |
| 5,020,527 A | 6/1991 | Dessertine |
| 5,031,610 A | 7/1991 | Armstrong |
| 5,042,685 A | 8/1991 | Moulding, Jr. |
| 5,049,345 A | 9/1991 | Collette |
| 5,069,204 A | 12/1991 | Smith |
| 5,119,806 A | 6/1992 | Palson |
| 5,152,456 A | 10/1992 | Ross |
| 5,184,761 A | 2/1993 | Lee |
| 5,193,745 A | 3/1993 | Holm |
| 5,217,004 A | 6/1993 | Blasnik |
| 5,239,992 A | 8/1993 | Bougamont |
| 5,261,601 A | 11/1993 | Ross |
| 5,273,172 A | 12/1993 | Rossbach |
| 5,295,479 A | 3/1994 | Lankinen |
| 5,299,701 A | 4/1994 | Barker |
| 5,347,998 A | 9/1994 | Hodson |
| 5,388,572 A | 2/1995 | Mulhauser |
| 5,408,994 A | 4/1995 | Wass |
| 5,415,161 A | 5/1995 | Ryder |
| 5,421,482 A | 6/1995 | Garby |
| 5,482,030 A | 1/1996 | Klein |
| 5,487,378 A | 1/1996 | Robertson |
| 5,501,375 A | 3/1996 | Nilson |
| 5,511,540 A | 4/1996 | Bryant |
| 5,544,647 A | 8/1996 | Jewett |
| 5,544,657 A | 8/1996 | Kurowski |
| 5,546,932 A | 8/1996 | Galli |
| 5,549,101 A | 8/1996 | Trofast |
| 5,549,226 A | 8/1996 | Kopp |
| 5,564,414 A | 10/1996 | Walker |
| 5,611,444 A | 3/1997 | Garby |
| 5,622,163 A | 4/1997 | Jewett |
| 5,623,920 A | 4/1997 | Bryant |
| 5,645,050 A | 7/1997 | Zierenberg |
| 5,682,875 A | 11/1997 | Blower |
| 5,692,492 A | 12/1997 | Bruna |
| 5,718,355 A | 2/1998 | Garby |
| 5,772,085 A | 6/1998 | Bryant |
| 5,794,612 A | 8/1998 | Wachter |
| 5,809,997 A | 9/1998 | Wolf |
| 5,839,429 A | 11/1998 | Marnfeldt |
| 5,878,917 A | 3/1999 | Reinhard |
| 5,960,609 A | 10/1999 | Abrams |
| 5,988,496 A | 11/1999 | Bruna |
| 5,996,577 A | 12/1999 | Ohki |
| 6,014,970 A | 1/2000 | Ivri |
| 6,085,742 A | 7/2000 | Wachter |
| 6,142,146 A | 11/2000 | Abrams |
| 6,148,815 A | 11/2000 | Wolf |
| 6,149,054 A | 11/2000 | Cirrillo |
| 6,152,130 A | 11/2000 | Abrams |
| 6,164,494 A | 12/2000 | Marelli |
| 6,196,218 B1 | 3/2001 | Voges |
| 6,202,642 B1 | 3/2001 | McKinnon |
| 6,234,168 B1 | 5/2001 | Bruna |
| 6,240,918 B1 | 6/2001 | Ambrosio |
| 6,253,762 B1 | 7/2001 | Britto |
| 6,260,549 B1 | 7/2001 | Sosiak |
| 6,283,365 B1 | 9/2001 | Bason |
| 6,318,361 B1 | 11/2001 | Sosiak |
| 6,325,062 B1 | 12/2001 | Sosiak |
| 6,336,453 B1 | 1/2002 | Scarrott |
| 6,354,290 B1 | 3/2002 | Howlett |
| 6,357,442 B1 | 3/2002 | Casper |
| 6,360,739 B1 | 3/2002 | Rand |
| 6,397,839 B1 | 6/2002 | Stradella |
| 6,405,727 B1 | 6/2002 | MacMichael |
| 6,415,784 B1 | 7/2002 | Christrup |
| 6,422,234 B1 | 7/2002 | Bacon |
| 6,425,392 B1 | 7/2002 | Sosiak |
| 6,427,683 B1 | 8/2002 | Drachmann |
| 6,431,168 B1 | 8/2002 | Rand |
| 6,435,372 B1 | 8/2002 | Blacker |
| 6,439,227 B1 | 8/2002 | Myrman |
| 6,443,146 B1 | 9/2002 | Voges |
| 6,446,627 B1 | 9/2002 | Bowman |
| 6,460,537 B1 | 10/2002 | Bryant |
| 6,470,884 B2 | 10/2002 | Horlin |
| 6,474,331 B1 | 11/2002 | Rand |
| 6,510,847 B1 | 1/2003 | Helgesson |
| 6,516,799 B1 | 2/2003 | Greenwood |
| 6,546,928 B1 | 4/2003 | Ashurst |
| 6,553,988 B1 | 4/2003 | Holroyd |
| 6,581,590 B1 | 6/2003 | Genova |
| 6,596,260 B1 | 7/2003 | Brugger |
| 6,601,582 B2 | 8/2003 | Rand |
| 6,615,827 B2 | 9/2003 | Greenwood |
| 6,655,371 B2 | 12/2003 | Gallops |
| 6,655,379 B2 | 12/2003 | Clark |
| 6,659,307 B1 | 12/2003 | Stradella |
| 6,672,304 B1 | 1/2004 | Casper |
| 6,729,330 B2 | 5/2004 | Scarrott |
| 6,745,761 B2 | 6/2004 | Christrup |
| 6,752,145 B1 | 6/2004 | Bonney |
| 6,752,153 B1 | 6/2004 | Eckert |
| 6,755,190 B2 | 6/2004 | Rasmussen |
| 6,759,108 B1 | 7/2004 | Ota |
| 6,766,220 B2 | 7/2004 | McRae |
| 6,805,116 B2 | 10/2004 | Hodson |
| 6,823,863 B2 | 11/2004 | Huxham et al. |
| 6,860,262 B2 | 3/2005 | Christrup et al. |
| 6,866,037 B1 | 3/2005 | Aslin |
| 6,866,038 B2 | 3/2005 | Bacon |
| 6,889,687 B1 | 5/2005 | Olsson |
| 6,907,876 B1 | 6/2005 | Clark |
| 6,926,002 B2 | 8/2005 | Scarrott |
| 7,007,689 B2 | 3/2006 | Burns |
| 7,036,505 B2 | 5/2006 | Bacon |
| 7,047,964 B2 | 5/2006 | Bacon |
| 7,047,967 B2 | 5/2006 | Knudsen |
| 7,072,738 B2 | 7/2006 | Bonney |
| 7,093,594 B2 | 8/2006 | Harrison |
| 7,100,530 B2 | 9/2006 | Lu |
| 7,107,986 B2 | 9/2006 | Rand |
| 7,147,170 B2 | 12/2006 | Nguyen |
| 7,167,776 B2 | 1/2007 | Maharajh |
| 7,191,918 B2 | 3/2007 | Ouyang |
| 7,195,134 B2 | 3/2007 | Ouyang |
| 7,219,664 B2 | 5/2007 | Ruckdeschel |
| 7,225,805 B2 | 6/2007 | Bacon |
| 7,234,460 B2 | 6/2007 | Greenleaf |
| 7,237,727 B2 | 7/2007 | Wang |
| 7,270,124 B2 | 9/2007 | Rasmussen |
| 7,275,660 B2 | 10/2007 | Stradella |
| 7,296,567 B2 | 11/2007 | Mahon |
| 7,299,800 B2 | 11/2007 | Stradella |
| 7,299,801 B2 | 11/2007 | Hodson |
| 7,306,116 B2 | 12/2007 | Fuchs |
| 7,318,434 B2 | 1/2008 | Gumaste |
| 7,322,352 B2 | 1/2008 | Minshull |
| 7,331,340 B2 | 2/2008 | Barney |
| 7,334,577 B2 | 2/2008 | Gumaste |

(56) References Cited

U.S. PATENT DOCUMENTS

| | | |
|---|---|---|
| 7,341,057 B2 | 3/2008 | Scarrott |
| 7,347,200 B2 | 3/2008 | Jones |
| 7,347,202 B2 | 3/2008 | Aslin |
| 7,367,333 B2 | 5/2008 | Hodson |
| 7,387,121 B2 | 6/2008 | Harvey |
| 7,400,940 B2 | 7/2008 | McRae |
| 7,418,961 B2 | 9/2008 | Jones |
| 7,448,342 B2 | 11/2008 | von Schuckmann |
| 7,454,267 B2 | 11/2008 | Bonney |
| 7,497,214 B2 | 3/2009 | Hodson |
| 7,510,100 B2 | 3/2009 | Stradella |
| 7,597,099 B2 | 10/2009 | Jones |
| 7,637,260 B2 | 12/2009 | Holroyd |
| 7,743,765 B2 | 6/2010 | Hodson |
| 8,181,591 B1 * | 5/2012 | Gulka et al. ............ 116/285 |
| 2001/0013342 A1 | 8/2001 | Burns |
| 2001/0013343 A1 | 8/2001 | Andersson |
| 2001/0025639 A1 | 10/2001 | Christrup |
| 2001/0032644 A1 | 10/2001 | Hodson |
| 2002/0000225 A1 | 1/2002 | Schuler |
| 2002/0011247 A1 | 1/2002 | Ivri |
| 2002/0026938 A1 | 3/2002 | Hodson |
| 2002/0043262 A1 | 4/2002 | Langford |
| 2002/0088458 A1 | 7/2002 | Christrup et al. |
| 2002/0100473 A1 | 8/2002 | Christrup et al. |
| 2002/0104530 A1 | 8/2002 | Ivri |
| 2002/0104532 A1 | 8/2002 | Christrup |
| 2002/0139812 A1 | 10/2002 | Scarrott |
| 2002/0189611 A1 | 12/2002 | Greenwood |
| 2003/0033055 A1 | 2/2003 | McRae |
| 2003/0065149 A1 | 4/2003 | McGinnis |
| 2003/0089368 A1 | 5/2003 | Zhao |
| 2003/0100867 A1 | 5/2003 | Fuchs |
| 2003/0106550 A1 | 6/2003 | Harvey |
| 2003/0116155 A1 | 6/2003 | Rasmussen |
| 2003/0136401 A1 | 7/2003 | Jansen |
| 2003/0138559 A1 | 7/2003 | Ashurst |
| 2003/0150448 A1 | 8/2003 | Bacon |
| 2003/0178021 A1 | 9/2003 | Rasmussen |
| 2003/0183225 A1 | 10/2003 | Knudsen |
| 2003/0183226 A1 | 10/2003 | Brand |
| 2003/0192535 A1 | 10/2003 | Christrup |
| 2003/0207057 A1 | 11/2003 | Britto |
| 2003/0230305 A1 | 12/2003 | Christrup |
| 2004/0005475 A1 | 1/2004 | Curie |
| 2004/0020486 A1 | 2/2004 | Huxham |
| 2004/0025867 A1 | 2/2004 | Holroyd |
| 2004/0025868 A1 | 2/2004 | Bruna |
| 2004/0025870 A1 | 2/2004 | Harrison |
| 2004/0055596 A1 | 3/2004 | Bacon |
| 2004/0065320 A1 | 4/2004 | Bacon |
| 2004/0065326 A1 | 4/2004 | MacMichael |
| 2004/0069301 A1 | 4/2004 | Bacon |
| 2004/0079362 A1 | 4/2004 | Christrup |
| 2004/0089299 A1 | 5/2004 | Bonney |
| 2004/0107962 A1 | 6/2004 | Harrison |
| 2004/0129793 A1 | 7/2004 | Nguyen |
| 2004/0134488 A1 | 7/2004 | Davies |
| 2004/0134489 A1 | 7/2004 | Burns |
| 2004/0134824 A1 | 7/2004 | Chan |
| 2004/0139965 A1 | 7/2004 | Greenleaf |
| 2004/0139966 A1 | 7/2004 | Hodson |
| 2004/0144798 A1 | 7/2004 | Ouyang |
| 2004/0149772 A1 | 8/2004 | Ouyang |
| 2004/0149773 A1 | 8/2004 | Ouyang |
| 2004/0172162 A1 | 9/2004 | Bonney |
| 2004/0187865 A1 | 9/2004 | Ashurst |
| 2004/0230286 A1 | 11/2004 | Moore |
| 2005/0016528 A1 | 1/2005 | Aslin |
| 2005/0076904 A1 | 4/2005 | Jones |
| 2005/0081846 A1 | 4/2005 | Barney |
| 2005/0087191 A1 | 4/2005 | Morton |
| 2005/0121024 A1 | 6/2005 | Langford |
| 2005/0126469 A1 | 6/2005 | Lu |
| 2005/0143866 A1 | 6/2005 | McRae |
| 2005/0183724 A1 | 8/2005 | Gumaste |
| 2005/0205512 A1 | 9/2005 | Scarrott |
| 2005/0209558 A1 | 9/2005 | Marx |
| 2005/0263612 A1 | 12/2005 | Wang |
| 2006/0011197 A1 | 1/2006 | Hodson |
| 2006/0037611 A1 | 2/2006 | Mahon |
| 2006/0047368 A1 | 3/2006 | Maharajh |
| 2006/0060192 A1 | 3/2006 | Lu |
| 2006/0071027 A1 | 4/2006 | Davies |
| 2006/0131346 A1 | 6/2006 | Purkins et al. |
| 2006/0151524 A1 | 7/2006 | Stradella |
| 2006/0163275 A1 | 7/2006 | Stradella |
| 2006/0174869 A1 | 8/2006 | Gumaste |
| 2006/0186223 A1 | 8/2006 | Wang |
| 2006/0213505 A1 | 9/2006 | Hodson |
| 2006/0213506 A1 | 9/2006 | Hodson |
| 2006/0213510 A1 | 9/2006 | Hodson |
| 2006/0231093 A1 | 10/2006 | Burge |
| 2006/0237002 A1 | 10/2006 | Bonney |
| 2006/0237009 A1 | 10/2006 | Jones et al. |
| 2006/0243275 A1 | 11/2006 | Ruckdeschel |
| 2006/0254581 A1 | 11/2006 | Genova |
| 2006/0278225 A1 | 12/2006 | MacMichael et al. |
| 2006/0283444 A1 | 12/2006 | Jones |
| 2006/0289005 A1 | 12/2006 | Jones et al. |
| 2006/0289008 A1 | 12/2006 | Rand |
| 2007/0017511 A1 | 1/2007 | Ohki |
| 2007/0029341 A1 | 2/2007 | Stradella |
| 2007/0051745 A1 | 3/2007 | Poulard |
| 2007/0056502 A1 | 3/2007 | Lu |
| 2007/0056580 A1 | 3/2007 | Jones |
| 2007/0056585 A1 | 3/2007 | Davies |
| 2007/0062518 A1 | 3/2007 | Geser |
| 2007/0062522 A1 | 3/2007 | Bacon |
| 2007/0089735 A1 | 4/2007 | Langford |
| 2007/0119450 A1 | 5/2007 | Wharton |
| 2007/0144514 A1 | 6/2007 | Yeates |
| 2007/0163576 A1 | 7/2007 | Bacon |
| 2007/0181120 A1 | 8/2007 | Wright |
| 2007/0181123 A1 | 8/2007 | Houzego |
| 2007/0194041 A1 | 8/2007 | Stradella |
| 2007/0210102 A1 | 9/2007 | Stradella |
| 2007/0241136 A1 | 10/2007 | Poulard |
| 2007/0246042 A1 | 10/2007 | Purkins et al. |
| 2007/0251950 A1 | 11/2007 | Bacon |
| 2007/0284383 A1 | 12/2007 | Wright |
| 2008/0017189 A1 | 1/2008 | Ruckdeschel |
| 2008/0017193 A1 | 1/2008 | Jones |
| 2008/0035144 A1 | 2/2008 | Bowman |
| 2008/0041877 A1 | 2/2008 | Stradella |
| 2008/0047556 A1 | 2/2008 | Hodson |
| 2008/0060643 A1 | 3/2008 | Hodson |
| 2008/0066742 A1 | 3/2008 | Hodson |
| 2008/0092887 A1 | 4/2008 | Hodson |
| 2008/0107848 A1 | 5/2008 | Bacon |
| 2008/0115784 A1 | 5/2008 | Gumaste |
| 2008/0135575 A1 | 6/2008 | Ingram |
| 2008/0135576 A1 | 6/2008 | Bacon |
| 2008/0173301 A1 | 7/2008 | Deaton |
| 2008/0210224 A1 | 9/2008 | Brunnberg |
| 2008/0210226 A1 | 9/2008 | Butterworth |
| 2008/0251004 A1 | 10/2008 | Stradella |
| 2008/0283541 A1 | 11/2008 | Warby |
| 2008/0314383 A1 | 12/2008 | Barney |
| 2009/0114219 A1 | 5/2009 | Ferris |
| 2009/0211578 A1 | 8/2009 | Fletcher |
| 2009/0229604 A1 | 9/2009 | Pearson |
| 2009/0229607 A1 | 9/2009 | Brunnberg |
| 2009/0293870 A1 | 12/2009 | Brunnberg et al. |
| 2009/0308385 A1 | 12/2009 | Brewer |
| 2009/0308389 A1 | 12/2009 | Pocock |
| 2010/0012115 A1 | 1/2010 | Bacon |
| 2010/0065050 A1 | 3/2010 | Holroyd |

(56) References Cited

U.S. PATENT DOCUMENTS

| | | | |
|---|---|---|---|
| 2010/0274198 A1* | 10/2010 | Bechtold | 604/189 |
| 2011/0311138 A1 | 12/2011 | Williams | |
| 2012/0020002 A1 | 1/2012 | Mathew | |

FOREIGN PATENT DOCUMENTS

| | | |
|---|---|---|
| AU | 2003234748 | 9/2003 |
| CN | 101247897 A | 8/2008 |
| DE | 629163 | 4/1936 |
| DE | 1077932 | 3/1960 |
| DE | 8715223 U | 2/1988 |
| DE | 4111895 | 10/1992 |
| DE | 19745513 | 4/1999 |
| DE | 29818662 U | 3/2000 |
| DE | 10061723 C | 7/2002 |
| DE | 202004021188 U | 3/2007 |
| EP | 0428380 B | 5/1991 |
| EP | 0501365 | 9/1992 |
| EP | 0629563 A | 12/1994 |
| EP | 1003583 B | 5/2000 |
| EP | 1019125 B | 7/2000 |
| EP | A-1201423 | 5/2002 |
| EP | 1229953 B | 8/2002 |
| EP | A-0820322 | 5/2004 |
| EP | 1443997 B | 8/2004 |
| EP | 1 169 245 | 8/2006 |
| EP | 1 316 365 B1 | 12/2006 |
| EP | 0883415 B | 12/2008 |
| FR | 2654627 | 5/1991 |
| FR | 2660630 | 10/1991 |
| FR | 2701653 | 8/1994 |
| GB | 161969 | 7/1922 |
| GB | 2385640 | 9/1945 |
| GB | 939324 | 10/1963 |
| GB | 1026763 | 4/1966 |
| GB | 1270272 | 4/1972 |
| GB | 2195544 | 4/1988 |
| GB | 2262452 A | 6/1993 |
| GB | 2263873 | 8/1993 |
| GB | 2264238 A | 8/1993 |
| GB | 2266466 A | 11/1993 |
| GB | 2278979 B | 1/1995 |
| GB | 2278979 B | 1/1995 |
| GB | 2279571 A | 1/1995 |
| GB | 2292891 A | 3/1996 |
| GB | 2 279 879 | 10/1997 |
| GB | 2 348 928 | 10/2000 |
| GB | 2366519 B | 3/2002 |
| GB | 2 372 543 | 8/2002 |
| GB | 2 372 542 | 8/2003 |
| GB | 2398250 A | 8/2004 |
| GB | 2398251 A | 8/2004 |
| GB | 2 381 201 | 2/2005 |
| GB | 2429166 A | 2/2007 |
| JP | 56-155759 | 12/1981 |
| JP | 57-75855 | 5/1982 |
| JP | 63251880 | 10/1988 |
| JP | 2003-056254 | 2/2003 |
| JP | 2003-508166 | 3/2003 |
| JP | 2009-505703 | 2/2009 |
| WO | WO 92/07599 | 5/1992 |
| WO | WO 92/07600 | 5/1992 |
| WO | WO 93/03783 | 3/1993 |
| WO | WO 93/24167 | 12/1993 |
| WO | WO 94/05359 | 3/1994 |
| WO | WO 94/19042 | 9/1994 |
| WO | WO 95/08484 | 3/1995 |
| WO | WO 96/39337 | 12/1996 |
| WO | WO 97/11296 | 3/1997 |
| WO | WO 97/30743 A2 | 8/1997 |
| WO | WO 98/01822 | 1/1998 |
| WO | WO 99/06091 | 2/1999 |
| WO | WO 99/06092 | 2/1999 |
| WO | WO 99/36116 | 7/1999 |
| WO | WO 01/17597 A1 | 3/2001 |
| WO | WO 01/31578 | 5/2001 |
| WO | WO 01/34231 A1 | 5/2001 |
| WO | WO 01/37909 | 5/2001 |
| WO | WO 02/16235 | 2/2002 |
| WO | WO02/24552 | 3/2002 |
| WO | WO 02/38207 | 5/2002 |
| WO | WO 02/43794 | 6/2002 |
| WO | WO 03/035155 A1 | 5/2003 |
| WO | WO 03/080161 | 10/2003 |
| WO | WO 2004/041339 A2 | 5/2004 |
| WO | WO 2004/073776 | 9/2004 |
| WO | WO 2004/089451 | 10/2004 |
| WO | WO 2004/096329 | 11/2004 |
| WO | WO 2006/054083 | 5/2006 |
| WO | WO 2006/062449 | 6/2006 |
| WO | WO 2006/119766 | 11/2006 |
| WO | WO 2007/012854 | 2/2007 |
| WO | WO 2007/022898 | 3/2007 |
| WO | WO 2007/029019 | 3/2007 |
| WO | WO 2007/034237 | 3/2007 |
| WO | WO 2007/066140 | 6/2007 |
| WO | WO 2007/077450 | 7/2007 |
| WO | WO 2007/103712 | 9/2007 |
| WO | WO 2007/107431 | 9/2007 |
| WO | WO 2007/141520 | 12/2007 |
| WO | WO 2008/025087 | 3/2008 |
| WO | WO 2008/040772 | 4/2008 |
| WO | WO 2008/079350 | 7/2008 |
| WO | WO 2008/079360 | 7/2008 |
| WO | WO 2008/087369 | 7/2008 |
| WO | WO 2008/104366 | 9/2008 |
| WO | WO 2008/119552 | 10/2008 |
| WO | WO 2008/148864 | 12/2008 |

OTHER PUBLICATIONS

Written Opinion of the International Searching Authority for PCT/GB2010/050405 mailed Jun. 16, 2010.
Rejection Decision dated Feb. 25, 2011, from copending Japanese Application No. 2007-547614, citing JP 57-75855 and JP 56-155759 (one page).
"Polyethylene—linear low density (LLDPE) CAS No. 9002-88-4" http://www.icis.com/v2/chemicals/9076159/polyethylene-linear-low-density.html (Jan. 19, 2011).
Japanese Office Action dated Sep. 24, 2010, issued in corresponding Japanese Application No. 2007-547614 (in English)—6 pages.
International Search Report for PCT/GB2005/004834 mailed May 2, 2006.
Definition of "mouth"; http://www.merriam-webster.com/dictionary/mouth; 2011.
U.S. Appl. No. 13/138,591, filed Jan. 2012, Bacon et al.

* cited by examiner

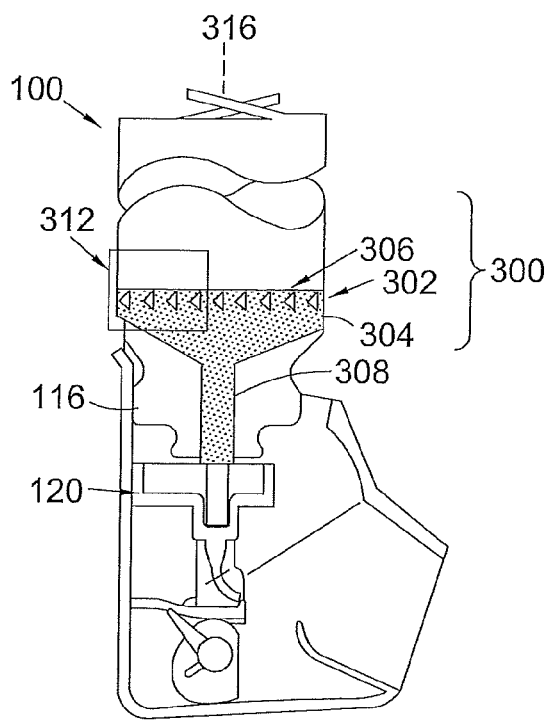
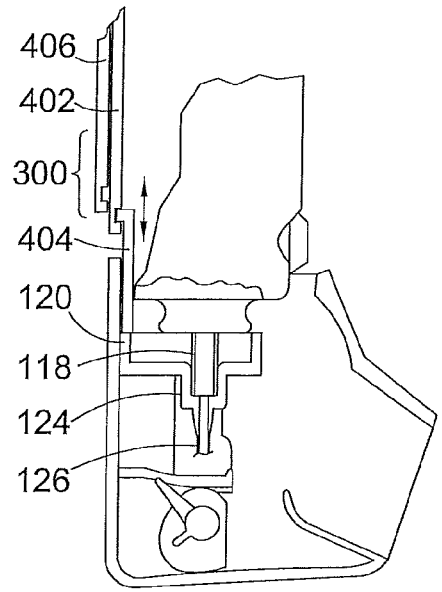
Figure 3
Figure 4
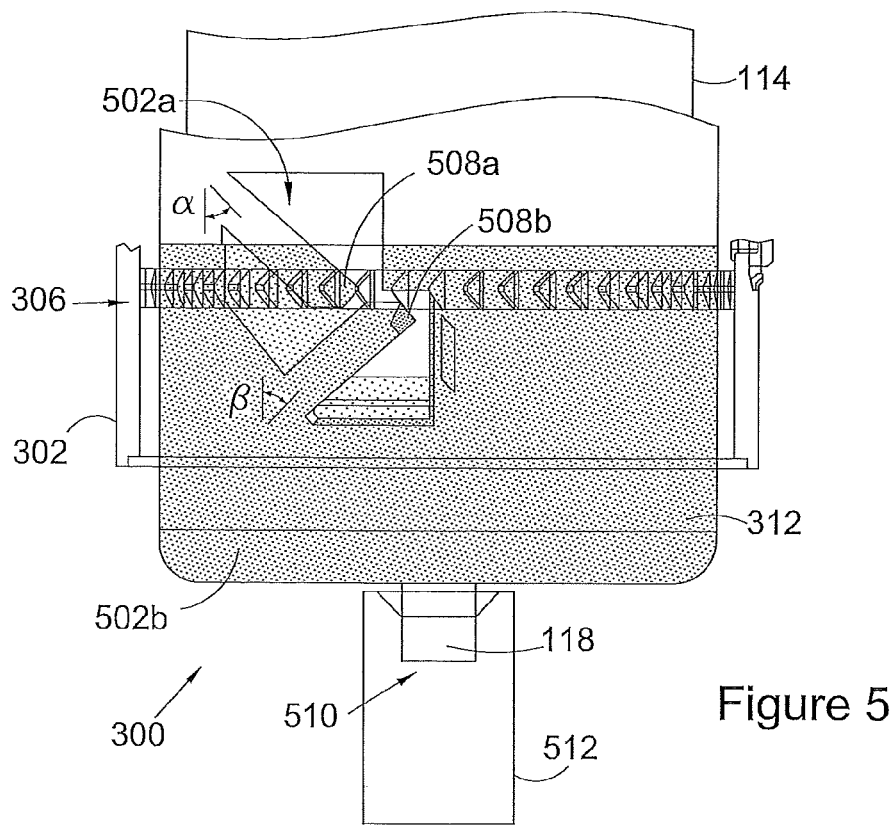
Figure 5

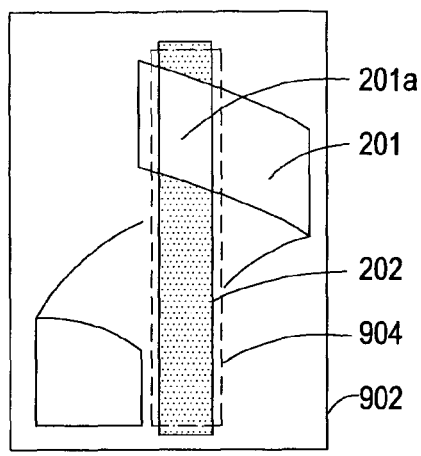
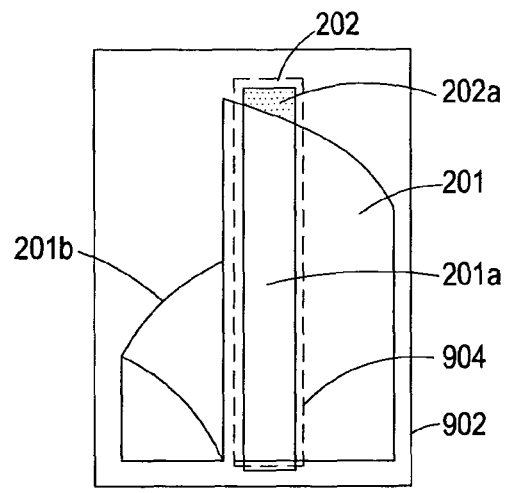
Figure 12          Figure 13
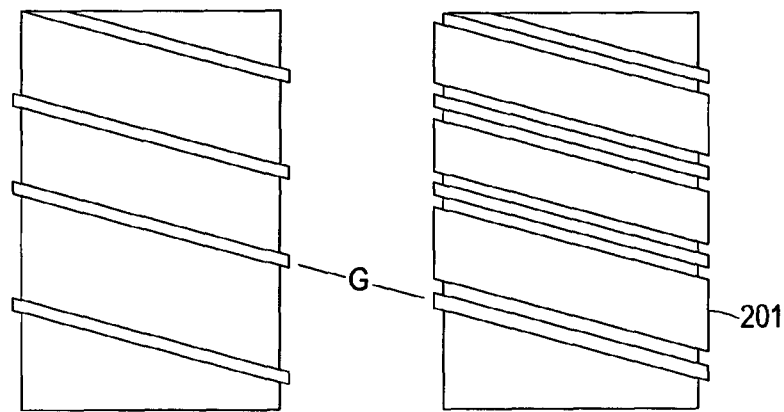
Figure 14

COUNTER

This application is the U.S. national phase of International Application No. PCT/GB2010/050405 filed 10 Mar. 2010 which designated the U.S. and claims priority to GB Application No. 0904059.3 filed 10 Mar. 2009, the entire contents of each of which are hereby incorporated by reference.

FIELD OF THE INVENTION

This invention generally relates to counters and in particular to counters for use with dispensers and to dispensers comprising said counters. More particularly the present invention relates to counters for use with metered-dose dispensers, such as metered-dose inhalers (MDIs).

BACKGROUND TO THE INVENTION

Counters are useful in a wide variety of applications, and are especially important in the field of medical dispensers where an accurate determination of the number of doses of medicament remaining in a medicament container might otherwise be difficult to obtain. An example of such a medical dispenser is a metered-dose inhaler.

Metered-dose inhalers (MDIs) are devices for dispensing medicaments, e.g. in aerosol form, to the lungs. Broadly speaking dispensers such as MDIs are comprised of two components: a container and a delivery device. The container holds the medication, e.g. dissolved or suspended in a propellant under high pressure to maintain a liquid phase. Additionally the container often comprises an internal metering valve, which is designed to release a precisely measured, reproducible dose of medicament when the valve is actuated. The delivery device typically includes an actuator and a mouthpiece. The actuator, which can be triggered by the user, for example by inhalation or manual operation, typically interacts with the metering valve of the container to induce release of a dose. The mouthpiece serves to direct the medication towards the user. FIG. 1 provides a view of a breath actuated dispenser and will be discussed in more detail below.

As medicament containers are typically made of an opaque material such as aluminium, and may be housed entirely within a delivery device, it is generally not possible for a user to gauge effectively how many doses of medicament remain therein. This may result in a user prematurely discarding a MDI still containing doses of medicament or worse using the MDI beyond its recommended lifetime. Neither situation is desirable—the former is wasteful while the latter is potentially dangerous. Users sometimes shake MDIs to try to obtain a measure of whether any medicament is present therein, but this only provides a very crude qualitative measure of the container contents. It would not, for example, enable a user to distinguish between a container comprising enough medicament and propellant to form a dose and one comprising a quantity of medicament and propellant that is less than that needed to fill the metering valve. In other words, there is a risk that users overestimate the amount of medicament present in a container and mistakenly conclude that there is sufficient medicament remaining for another dose when in fact there is not. Additionally a user may not be provided with sufficient warning to obtain a replacement medicament container prior to the one in use running out.

It is therefore desirable to provide dispensers, e.g. inhalers, with a counter mechanism that enables a user to track how many doses have been dispensed therefrom and, complementarily, how many doses remain. Indeed, regulatory bodies such as the Food and Drug Administration (FDA) of the United States and the European Medicines Agency (EMEA) have issued guidelines encouraging the implementation of dose-counters (Food and Drug Administration, "Guidance for industry: integration of dose counting mechanisms into MDI drug products", 2003; European Agency for Evaluation of Medicinal Products, "Final guideline on the quality of inhalation and nasal products", 2005).

Dose counters can generally be classified according to the manner by which a 'count' is registered, these being mechanical counters comprised of a series of moving parts that respond to a movement or mechanical force resulting, for example, in a displacement of the container/housing; electronic counters having electrical circuitry to sense an event associated with an actuation such as sound, temperature or pressure change; and electro-mechanical counters which combine electrical and mechanical parts.

Some background prior art relating to dose counters includes: EP1169245 Dispensing Apparatus Comprising a Dosage Counting Device; PCT/GB97/03480 Inhaler Dose Counter; PCT/US1996/008418 Indicator Device Responsive to Axial Force; PCT/FR2004/001844 Improved Dose Indicator for Fluid Product Dispensing Device; GB2372542 Dosage Counting Device; PCT/CA04/001884 Indicating Device with Warning Dosage Indicator; PCT/US04/039926 Dose Counter for Dispensers; and U.S. Pat. No. 7,047,964 Dispenser for Medicament.

Although such devices have provided the advantage of being able to provide some measure of the number of doses of medicament dispensed from a container and/or the number of doses remaining therein, there remains room for improvement. In particular it has proven difficult to provide dose counters that reliably "count" the release of medicament doses from containers. The difficulty encountered is that a relatively small movement, typically of the metering valve stem, needs to be detected and translated into a count. This difficultly is exacerbated by the fact that manufacturing tolerances in the length of medicament containers means they do not have a consistent length. At the same time, it is highly undesirable for any movements to not be counted since this will lead to the counter indicating a higher number of doses remaining than is actually the case. Moreover there is also regulatory pressure to minimise the number of false counts.

Additionally it is desirable that a counter, especially a medicament dose counter, display the count information in an easy to read form so it may be used by children and the elderly as well as adults. Naturally there is also a need that the counter can be manufactured at low cost.

SUMMARY OF THE INVENTION

Viewed from a first aspect the present invention provides a counter comprising:
 a first member disposed in at least a partial helical turn about a longitudinal axis of an entity whose movements and/or contents are to be counted, said first member having an indicium or indicia indicative of a count;
 a second member extending generally in the direction of said longitudinal axis, said second member being operatively disposed in overlapping relationship under and over one or more portions of said at least partial helical turn of said first member; and
 means to effect relative movement between said first and second members, said movement comprising a relative incremental rotation about said longitudinal axis.

In a preferred embodiment of the present invention the entity is a medicament container for a dispenser having a body for receiving the medicament container and a dispensing mechanism for dispensing a dose of medicament from the container.

In a further preferred embodiment of the present invention, the movement is performed in a relative incremental rotation in response to the dispenser being actuated.

In a still further preferred embodiment of the present invention, the indicium or indicia is or are indicative of the number of doses of medicament dispensed from, or remaining in, the container.

Thus viewed from a further aspect the present invention provides a dose counter for use with a dispenser having a body for receiving a medicament container and a dispensing mechanism for dispensing a dose of medicament from said container, the dose counter comprising:
  a first member disposed in at least a partial helical turn about a longitudinal axis of said medicament body and having an indicium or indicia indicative of the number of doses of medicament dispensed from, or remaining, in said container;
  a second member extending generally in the direction of said longitudinal axis, said second member being operatively disposed in overlapping relationship under and over one or more portions of said at least partial helical turns of said first member; and
  means to effect relative movement between said first and second members when said dispensing mechanism is actuated, said movement comprising a relative incremental rotation about said longitudinal axis.

In preferred embodiments of the present invention the first member is disposed in a plurality of helical turns (e.g. two or more) about said longitudinal axis of said dispenser In further preferred embodiments of the present invention the second member extends in a direction substantially parallel (e.g. parallel) to said longitudinal axis. Preferably the second member extends in a direction that is within 10°, still more preferably within 7°, e.g. within 5° or 1° of being parallel with said longitudinal axis.

In further preferred embodiments of the present invention, the relative incremental rotation about said longitudinal axis changes said overlapping relationship between said first and second members.

Viewed from another aspect the present invention provides a dose counter for use with a dispenser having a body for receiving a medicament container and a dispensing mechanism for dispensing a dose of medicament from said container, the dose counter comprising:
  a first member disposed in a single or partial helical turn about a longitudinal axis of said medicament container and having an indicium or indicia indicative of the number of doses of medicament dispensed from, or remaining, in said container;
  a housing having a window extending generally in the direction of said longitudinal axis, said housing being operatively disposed in overlapping relationship with said first member such that only one portion of said single or partial helical turn of said first member is exposed to said window; and
  means to effect relative movement between said first member and said housing when said dispensing mechanism is actuated, said movement comprising a relative incremental rotation about said longitudinal axis.

Viewed from a further aspect the present invention provides a dispenser comprising a counter as hereinbefore described.

More specifically the present invention provides a dispenser comprising:
  a body for receiving a medicament container;
  a medicament container;
  a dispensing mechanism for dispensing a dose of medicament from said container; and
  a counter as hereinbefore described.

In preferred embodiments, the counter comprises a dose counter for use with a dispenser having a body for receiving a medicament container and a dispensing mechanism for dispensing medicament from said container, wherein said container comprises a certain number of doses of medicament. As such, where reference is made to these features, it will be understood that they are only preferred and not essential to the invention.

The first member of the counter of the present invention preferably comprises a rigid, resilient or flexible material. The first member may be in the form of a helix per se or may be capable of being formed into a helix. The helix may or may not have a constant pitch. Regardless of the form of the first member, its helical shape readily lends itself to arrangement around cylindrical entities (e.g. containers) and thereby addresses the internal space constraints of, e.g. dispenser devices having such containers, without unduly increasing their bulkiness, i.e. diameter and length. For example, where the first member of the counter is to rotate during use without hindrance in a forward direction between an outer housing of the dispenser and an internal container, the first and second members may fit in a radial gap of less than about 5.0 mm, e.g. in a gap of 0.5 to 5 mm.

Furthermore, helical configurations may have a large ratio of total height to turn height, which provides increased display capacity. Helical configurations that may be useful in the counter of the present invention may comprise a partial turn (i.e. less than one complete helical turn), one or more complete helical turns or a combination of complete and partial helical turns. Broadly speaking, a complete helical turn comprises a 360-degree twist about an axis. The number of turns in the helix may depend on the indicia to be included thereon. The number of turns may therefore be in the range ½ to 12, preferably 1 to 8, e.g. 3 to 6.

In a preferred counter of the present invention, either the first member rotates and the second member is fixed or the second member rotates and the first member is fixed. Particularly preferably the second member is fixed and the first member rotates.

The second member of the counter may comprise a strip of flexible, resilient or rigid material. Thus, one or both of the first and second members may flex or bend to slide under and over each other. Preferably, one or both of the first and second members is comprised of a low friction coefficient material, for ease of sliding. Exemplary materials include acetal and PTFE-loaded acetal.

The first and second members are operatively disposed in an overlapping relationship. More specifically the second member is operatively disposed in overlapping relationship under and over one or more portions of said partial turn or turns of said first member. A preferred overlapping relationship is illustrated in FIG. 2, in which a dotted line indicates an imaginary boundary between two turns, and the arrow indicates the direction of rotation.

In FIG. 2(a) the second member 202 is under a portion of the first turn of the first member 201 and over portions of the second and third turns of the first member. Such an overlapping relationship therefore presents a portion 201a of the first turn, e.g. through a window indicated approximately by the dashed line. This serves to highlight the indicium on the portion 201a of the first turn of the first member while occluding from view the indicia on the other corresponding portions. In FIG. 2(b) there has been relative movement between the first and second members, which in operation may be caused by actuation of a dispensing mechanism. In FIG. 2(b) the second member is still under a portion 201b of the first turn of the first member and over portions of the second and third turns of the first member. A different indicium on the portion 201b of the first turn of the first member is, however, highlighted. In FIG. 2(c) there has been a number of relative movements between the first and second members which in operation may be caused by actuation of a dispensing mechanism. Thus in FIG. 2(c) the second member is now under a portion 201c of the second turn of the first member and over portions of the first and third turns of the first member.

In a preferred counter, the end of the first member that is displayed first is fed under the second member after one turn is completed. This may be achieved by biasing the first member to curl inwards or by using a means to feed the first member under the second member.

The afore-going describes a preferred overlapping relationship between the first and second members of the counter. Thus in a preferred counter said overlapping relationship is such that only a portion of one partial turn or turn of said first member lies over or under, preferably over, said second member. It will, however, be understood that other overlapping relationships are also possible.

Preferably the indicium or indicia is or are provided on, in or through the portion of said one partial turn or turn of said first member that is over or under, preferably over, said second member. Preferably the indicium or indicia is or are provided by a shape of the first member and/or indicia comprising one or more of: numbers, colours, letters or symbols. Symbols could include arrows or other pointing representations. Indicia may be oriented upright or horizontal with respect to the longitudinal axis of the dispenser, but are preferably upright.

Preferably the indicia at least comprise numbers. In particularly preferred counters, numeric indicia provide a quantitative measure of the amount of counts (e.g. doses released or, more preferably remaining in the dispenser). Preferred counters may, for example, provide a number resolution to the nearest half, one, two, ten, twenty, fifty, and/or a hundred, e.g. one or two. Fractions are of use, for example, when one dose of medicament corresponds to two or more actuations of a dispensing mechanism (e.g. 'puffs') by the user.

Where every other integer is represented this allows an increased font size to be used, thereby providing better legibility while having minimal or no effect in practice on a user's ability to track the count. In an alternative embodiment, the number resolution may increase as the count approaches its maximum (e.g. when the number of doses in a medicament container is becoming exhausted). This is beneficial for medicament containers containing hundreds of doses, where greater precision close to exhaustion is desirable. Alternatively, or additionally, colour coding may indicate whether the remaining amount of doses in the medicament container is 'high' (e.g. green) or 'low' (e.g. red). The indicia may be printed, cut out from, embossed, molded, adhered, incorporated, painted or otherwise marked (e.g. laser marked) on one or both of the first and second members.

In a further preferred embodiment of the counter and dispenser of the present invention, indicia may be provided on a window of the housing of the dispenser. This is preferably in addition to the indicia provided on the first member.

In preferred counters of the present invention, the first member helically disposed about the longitudinal axis of the entity, e.g. medicament container, has a substantially constant pitch and/or width along its length. However, in other counters these may vary along its length, e.g. in one or more discrete sections of different pitch/width along its length. It will be appreciated that a range of parameters of the first member, including the radius, height, number of turns, width and pitch (or equivalently helical angle), may be varied according to the preferences or requirements for a particular counter.

In a preferred embodiment of the counter of the present invention, there is provided a tubular sleeve around which the first member is disposed. The sleeve preferably surrounds the entity whose movements and/or contents are to be counted (e.g. the medicament container). For configurations in which the first member is rotated, there may be a tendency for the first member to contract inwards, particularly where the first member is disposed in a plurality of helical turns. This may eventually affect the ability of the first member to correctly rotate. The sleeve serves to counteract this contraction and helps the first member to maintain its shape.

In a further preferred embodiment of the counter of the present invention, there is provided a spine (e.g. a rigid spine) along at least a portion of the length of the first member. Alternatively, or additionally, the counter may comprise a guide element for guiding the first member. The guide element may therefore comprise a track mounted on, or integral with, another part of the dispenser or counter, e.g. the outer housing of the medicament or the afore-mentioned sleeve. The spine and/or guide element may help to correct any distortion experienced by the first member, such as a compression in an axial direction thereof, thereby minimising counting inaccuracies. However, the first member may correct itself naturally without the need for such a spine.

In a preferred counter of the present invention, the means to effect a relative rotation comprises a drive mechanism having a pawl-bearing member to releasably engage a teeth-bearing member. Broadly speaking, the drive mechanism translates vertical movements, e.g. of a junction member or medicament container, into rotational movements of a counter, e.g. of the first member. A relative rotation between the first and second members may be allowed in a forward direction but substantially prevented in a reverse direction. In this way, the counter cannot be improperly 'reset' (accidentally or deliberately), to provide a false indication of the count (e.g. number of doses) in the dispenser. This minimises the possibility of user abuse, and is of particular use for medicament dispensers. The counter may, however, be alternatively designed to allow for it to be rewound and/or for it to be reset by a manufacturer upon replacement with a fresh entity (e.g. medicament container).

In a further preferred counter, the drive mechanism biases the first, generally helical member in a rotational direction about the longitudinal axis responsive to a force in a direction parallel to the longitudinal axis. Such a force could be provided by a dispensing mechanism of a dispenser device. Preferably, a count is at least initiated before a corresponding unit of product comprising medicament is released, e.g. for inhalation.

It will be appreciated from the afore-going that the relative movement between the first and second members may be achieved by fixing the first member to the entity whose movement and/or contents are to be counted (e.g. a medicament container or tubular sleeve) and rotating the second member around said entity. Preferably, however, the second member is fixed to said entity (e.g. medicament container or tubular sleeve). Correspondingly it is also preferred that said first member rotates about said longitudinal axis of said entity. In this configuration, vertical movement of the first member per se does not cause a count to be made.

Rotation of the first or second member about the entity (e.g. medicament container) is preferably achieved by driving said first or second member by the drive mechanism, e.g. by fixing the first or second member to the pawl-bearing member or the tooth-bearing member, whichever one is rotating. Preferably said first member is driven by (e.g. attached to) said drive mechanism.

The dispenser may include a housing having a window in substantial superimposed alignment with the second member, with the overlapping relationship being such that only one portion of said at least a partial helical turn of said first member is exposed to the window. The window may be a hole in the housing or may be a transparent area of the housing. This allows a precise reading of the quantity of unit product, such as metered doses of medicament, remaining in the container or dispensed therefrom. Where the second member comprises a rigid strip of material, this could be mounted internally on, or be integral with, the housing.

It will be apparent from the afore-going discussion that the present invention finds particular application in dispensers, especially metered dose dispensers. Nevertheless, the present invention may be implemented in conjunction with any suitable device.

The counters of the present invention may be used with a conventional dispenser comprising a body for receiving a medicament container and a dispensing mechanism for dispensing a dose of medicament from the container. Preferably the dose counter is used with a metered dose inhaler. Particularly preferably the dose counter is used with a breath actuated metered dose inhaler. Such inhalers are known in the art, e.g. from WO 1998/41254 (U.S. Pat. No. 6,422,234), WO 2002/11802 (U.S. Pat. No. 7,036,505), WO 2002/058772 (U.S. Pat. No. 6,866,038) and WO 2004/073776 (U.S. 2007 062522), the contents of which are incorporated herein by reference.

BRIEF DESCRIPTION OF THE DRAWINGS

These and other aspects of the invention will now be further described, by way of example only, with reference to the accompanying figures in which:

FIG. 3 is a cross-sectional view of the dispenser of FIG. 1 to which a counter according to a first embodiment of the present invention has been attached;

FIG. 4 is a cross-sectional view of the dispenser of FIG. 1 to which a counter according to a first embodiment of the present invention has been attached;

FIG. 5 illustrates a drive mechanism for use with the counter of the present invention;

FIG. 12 schematically illustrates an overlapping relationship between members of the counter according to the present invention;

FIG. 13 schematically illustrate another overlapping relationship between members of the counter according to the present invention; and FIG. 14 schematically illustrates a guide element for guiding a first member.

DETAILED DESCRIPTION OF PREFERRED EMBODIMENTS

To explain the invention, a brief overview of some features and operating principles of exemplary dispensers is initially provided. As used herein the term "dispenser" is intended to mean any device suitable to receive a container holding a product (e.g. medicament), and which will also dispense the product from the container upon actuation.

Figure 1:
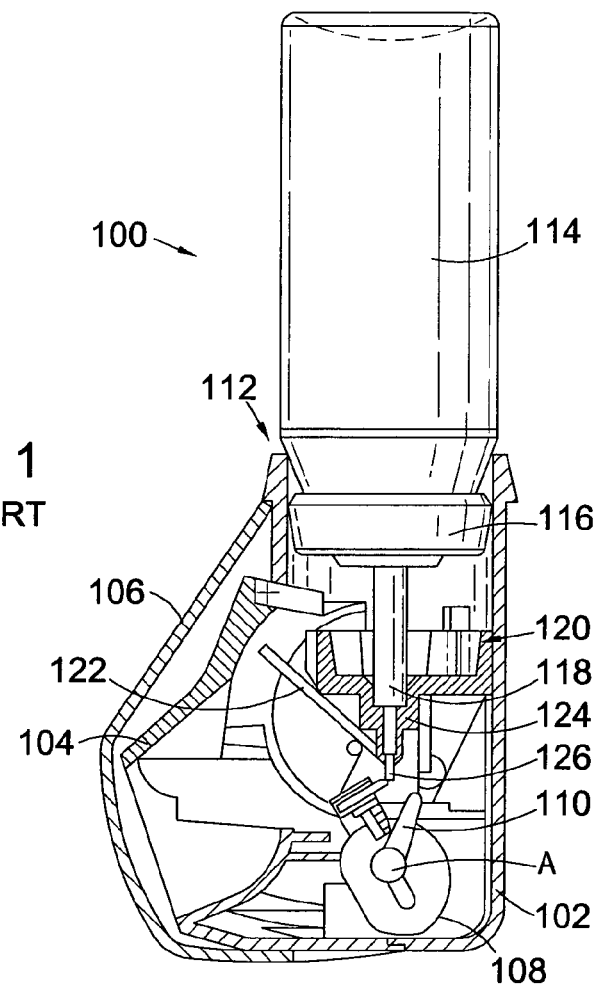
FIG. 1 is a cross-sectional view of a conventional dispenser to which a counter according to the present invention may be attached.
Figures 2A, 2B, 2C:
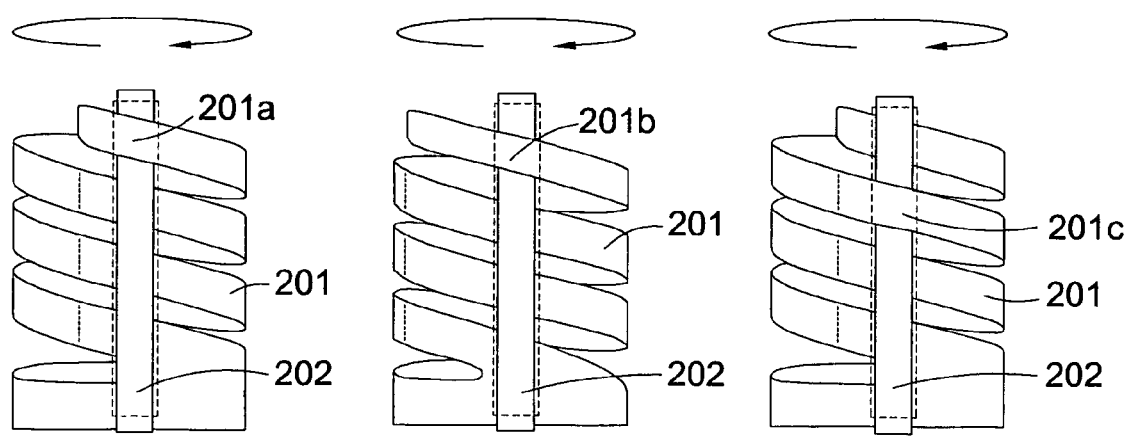
FIGS. 2(a) to 2(c) schematically illustrate an overlapping relationship between members of the counter according to the present invention.

FIG. 1 shows in partial cross section an example of a breath-actuated, kink valve dispenser. The dispenser 100 comprises a body 102 with a mouthpiece 104 and a pivoted mouthpiece cover 106. The mouthpiece cover is pivotable about an axis, A, low in the body and carried on a cam arrangement comprising two cam lobes (only one cam lobe 108 is shown), together with a central finger 110. The body has an opening 112 for receiving a medicament container 114. The container may be held fixedly in place at the upper end of the body, at a location where the body extends completely around a metering valve assembly of the container (not shown). The metering valve assembly comprises a metering chamber 116 and an outlet stem 118. Alternatively, or additionally, if the container is housed entirely within the dispenser, the container may be held at an end distal of its metering valve assembly, for example by a cap portion of an outer housing. In a preferred dispenser for use with the counter of the present invention, the dispenser comprises a tolerance adjustment mechanism (e.g. an abutment feature) as described in WO 2007/029019 (U.S. application Ser. No. 11/991,680).

Moulded inside the body, inwards of the opening 112 are internal grooves (not shown). A junction member 120 is slidably accommodated in the body with the grooves engaged by ribs in its periphery. The junction member has a pair of pivot clips (not shown) for pivotally locating the flap 122 in the junction member 120. Centrally, the junction member has a socket 124 for an outlet stem 118 of the container. The socket is continued by a passage 126, which has a thin wall, kinkable portion and a nozzle end. The nozzle end is in a movable part of the junction member. The main part and the movable part of the junction member are connected by a living hinge.

The moving part of the junction member 120 also carries a pair of sears (not shown) that are arranged to engage with latches on the underside of flap 122 as described below. The movable part of the junction member also carries a finger for engagement with the cam arrangement.

Initially when the dispenser is closed the flap is unlatched and the movable part of the junction member is in its lower position. The kinkable portion, sometimes referred to herein as a kinkable valve, is open. On opening of the mouthpiece cover 106, the central finger of the cam arrangement acts on the movable part of the junction member to close the kink valve. The movement of the movable part of the junction member also serves to engage the sears of the movable member with the latches of the flap, thereby fixing the flap in an upper position. The junction member 120 is also lifted by the main cam lobes 108 against an internal spring (not shown) of the metering valve assembly, with displacement of the stem 118 inwards of the container. Further lifting of the mouthpiece cover 106 opens the container valve and a metered dose is released into the upper part of the tube, the dose being retained by the closed kink valve acting as a closed valve.

Breathing in through the mouthpiece causes an air flow through the dispenser and impinges on flap 122. This causes release of the sears and the kink tube tends to straighten under the action of its own resilience and the pressure of the retained dose. The dose is thus released through the nozzle into the mouthpiece for inhalation. The flap may also carry a finger (not shown) that can act on the moveable part of the junction member to ensure that the kink valve is opened when the flap is breath actuated.

These and other features of exemplary dispensers are described in more detail in Clinical Designs Limited's prior PCT applications WO 1998/41254 (U.S. Pat. No. 6,422,234); WO 2002/11802 (U.S. Pat. No. 7,036,505); WO 2002/058772 (U.S. Pat. No. 6,866,038) and WO 2004/073776 (U.S. 2007 062522), the disclosures of all of which are fully incorporated herein by reference.

The following description of exemplary embodiments of the invention is presented in the context of metered-dose inhalers, in particular the dispenser illustrated in FIG. 1. However, as stated previously, it will be appreciated that this is but one example of a suitable application.

Referring to FIG. 3, the dispenser 100 may be provided with a teeth-bearing member 302 of a pawl-and-tooth drive mechanism 300. The term "drive mechanism" is to be interpreted broadly as any means by which the dispensing of a dose is linked to a counter being made by the counter. In described embodiments the dispensing of a dose will involve a vertical movement, e.g. of junction member 120, as described earlier with reference to FIG. 1. In the described preferred embodiment this vertical movement is translated into an incremental rotation that is counted.

The teeth-bearing member has a collar 304, which extends around the container just above the metering valve assembly, with a ring of moulded teeth 306 on an outwardly facing surface. A pair of arms 308 (only one is depicted in FIG. 3) extends downwardly from the collar on either side of the metering chamber 116. The arms can be spring-loaded against, or affixed to, an upper portion of junction member 120. An annular, pawl-bearing member 312 (depicted only in part in FIG. 3 for clarity) is configured and arranged to fit around the collar 304, for engagement with the teeth.

The junction member moves vertically, e.g. when a mouthpiece cover is opened. The action of lifting the junction member 120 (which causes the release of a dose from a pressurised medicament container) imparts an upward force on the teeth-bearing member in a direction parallel to a longitudinal axis 316 of the dispenser. The resulting upward displacement of the teeth-bearing collar leads to an engagement with pawl-bearing member 312, which is rotatably driven. Once a dose is released and the mouthpiece cover is rotated to a closed position, the junction and teeth-bearing members are able to move downwards to their original positions by means of, for example, an internal spring (not shown) of the container. This downward movement also leads to an engagement between teeth-bearing member 302 and pawl-bearing member 312, resulting in a further rotation.

Taken together, these two increments of rotation define a "complete" incremental rotation of the pawl-bearing member.

FIG. 4 illustrates an alternative exemplary embodiment in which a dispenser is provided with a pawl-bearing inner sleeve 402 coupled to an upper end of junction member 120 by an interlocking connecting rod 404. A ring of teeth is moulded on an inner surface of outer housing 406, which comprises a teeth-bearing member. The mode of operation is similar to that described above.

FIG. 5 illustrates an exemplary drive mechanism 300 in which the ring of teeth 306 is disposed on an inwardly facing surface of the teeth-bearing member 302, with the pawl-bearing member 312 being disposed within its bore.

Two pawls 502a, 502b, are borne integrally by pawl-bearing member 312, being defined by a cutaway portion thereof. Viewed from this perspective, each pawl extends toward the ring of teeth 306 in an annular plane of the pawl-bearing member 312, at about the same (but opposite) angle $\alpha$, $\beta$. The second (lower) pawl 502b is offset in a circumferential direction relative to the first (upper) pawl 502a. The pawls each have a root end and a free end. A tip 508a, 508b protrudes radially outwardly from each of the free ends, to operatively engage with the teeth.

The outlet stem 118 of the metering valve assembly (hidden from view) inserts down through the clearance hole of the base of the pawl-bearing member 312 to rest on a shelf 510 in a stem block 512. This differs from the preferred configuration shown in FIG. 3. It will be appreciated that this difference, in itself, is not of particular significance in the context of the drive mechanism.

In operation, and viewed from this perspective, the pawl-bearing member 312 moves up and down, and rotates, relative to the teeth-bearing member 302 when the stem block is moved upwards to depress 118 and release a dose. For convenience, the upward and downward movements of the pawl-bearing member 312 will be referred to as the 'count stroke' and 'return stroke', respectively.

Figure 6A:
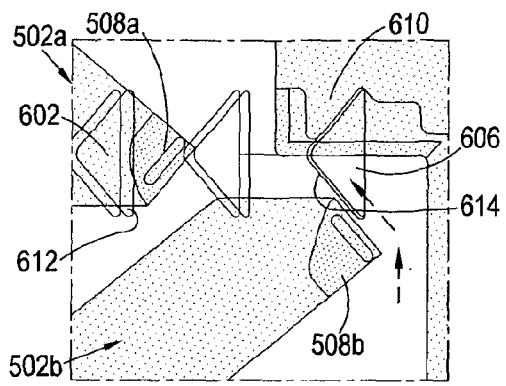
FIGS. 6a to 6d are schematic diagrams showing a part of the principle of operation of the drive mechanism for use with a counter of the present invention.
Figure 6B:
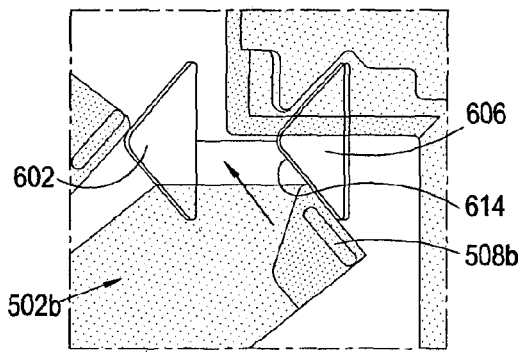
Figure 6C:
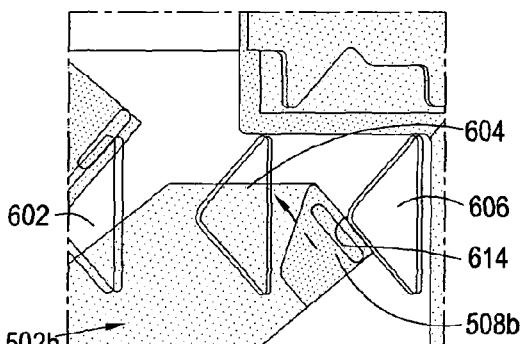
Figure 6D:
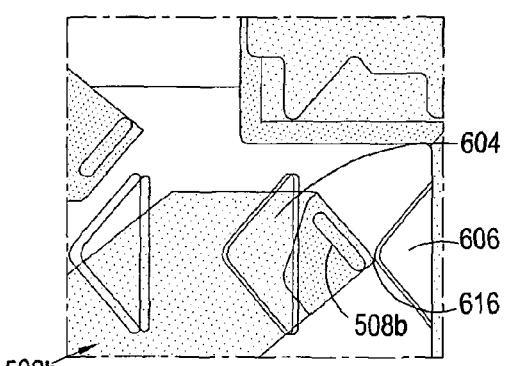

FIGS. 6a to 6d show a sequence of cross-sectional views of the drive mechanism during the count stroke. In FIG. 6a, the pawl-bearing member is at rest on the teeth by means of a protruding block 610. An upwardly directed force on the pawl-bearing member initially results in frictional engagement between the tip 508a of the first (upper) pawl 502a and a vertical face 612 of tooth 602. This action guides the pawl-bearing member substantially vertically upwards, until such a time as the tip 508b of the second (lower) pawl 502b engages with a lower, sloped face 614 of tooth 606 (FIG. 6b). This effects an upward diagonal movement, which proceeds until tip 508b reaches, and then surpasses, the apex 616 of tooth 606 (FIGS. 6c and 6d, respectively). At the same time, the first (upper) pawl 502a flexes slightly inwards to allow tip 508a to pass over tooth 602 (FIG. 6c). Dashed arrows indicate the direction of movement.

FIGS. 7a to 7d show a sequence of cross-sectional views of the drive mechanism during the return stroke. Like elements to those of FIG. 6 are indicated by like reference numbers.

Figure 7A:
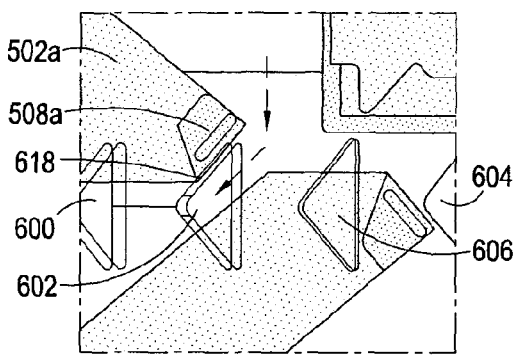
FIGS. 7a to 7d are schematic diagrams showing another part of the principle of operation of the drive mechanism for use with a counter of the present invention.
Figure 7B:
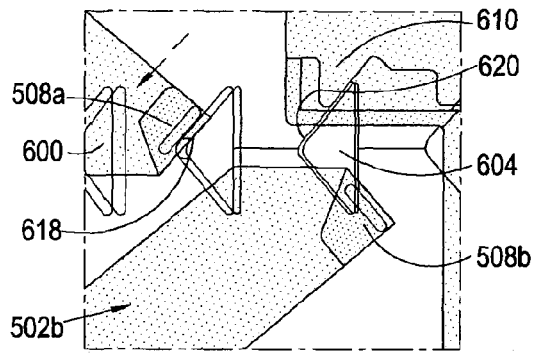
Figure 7C:
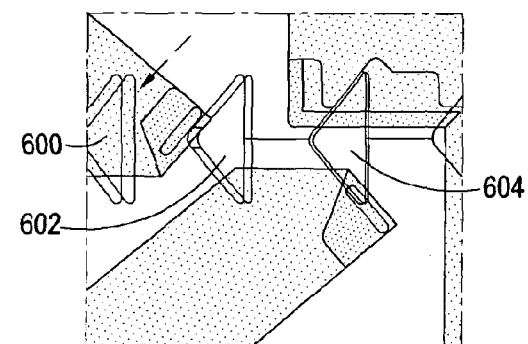
Figure 7D:
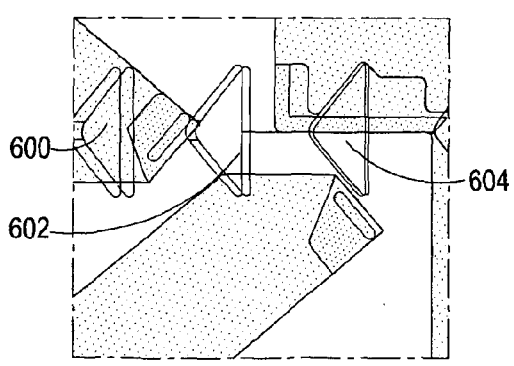

In FIG. 7a, which corresponds substantially to FIG. 6d, the tip 508a of the first (upper) pawl 502a moves vertically downwards until it frictionally engages with an upper, sloped face 618 of tooth 602, resulting in a downward diagonal movement. In FIG. 7b, the tip 508a has proceeded further down face 618, and block 610 now engages an upper, sloped face 620 of tooth 604. This time the second (lower) pawl 502b flexes slightly inwardly to allow tip 508b to pass over tooth 604. This proceeds until the pawl-bearing member again comes to rest on the teeth (FIGS. 7c and 7d). FIG. 7d corresponds substantially to FIG. 6a, but rotated by one tooth, i.e. from tooth 606 to tooth 604.

Although the foregoing discussion has described the case where the pawl-bearing member rotates about an axis (i.e. rotates relative to the dispenser as a whole), it is equally possible that the teeth-bearing member rotates.

It will also be appreciated that a rotational displacement need not be performed by way of two engagements (though this may be beneficial), nor need it comprise vertical and rotational movement. For example, a mechanism providing purely rotational motion, in other words without vertical movement, could also be used. However, the drive mechanism should effect a relative rotation between the first and second members of the counter about a longitudinal axis of the counter.

Figure 8:
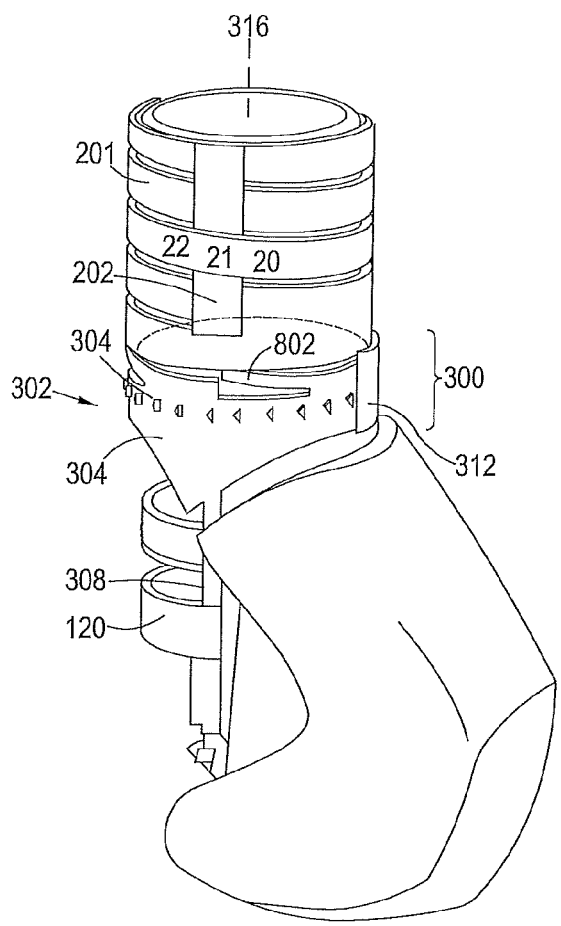
FIG. 8 is a perspective internal view of a dispenser including a counter according to the present invention.

In the specific embodiment of a dose counter shown in FIG. 8, a cantilever 802 extends upwardly from an upper edge of the collar 304 of a teeth-bearing member 302 and integrally connects to a second member 202 of the dose counter. The second member extends substantially vertically. In this particular configuration, the second member 202 is spatially fixed relative to the teeth-bearing member 302, which oscillates between a lower position and an upper position. The cantilever 802 allows the teeth-bearing member to move unobstructed and exerts a downward spring force on the collar 304 of the teeth-bearing member, causing it to return to its lower position. The dose counter also includes a generally helical first member 201 forming multiple turns around the container. The first member 201 is coupled to pawl-bearing member 312 (shown only in part). The second member 202 overlaps under and over the first member 201.

In operation, the rotation of pawl-bearing member 312, caused by the upward and subsequent downward displacements of the teeth-bearing member 302, acts to rotate the first member 201. For this particular drive mechanism, these displacements taken together define a rotation of the helical member from a first to a second position.

Figure 9:
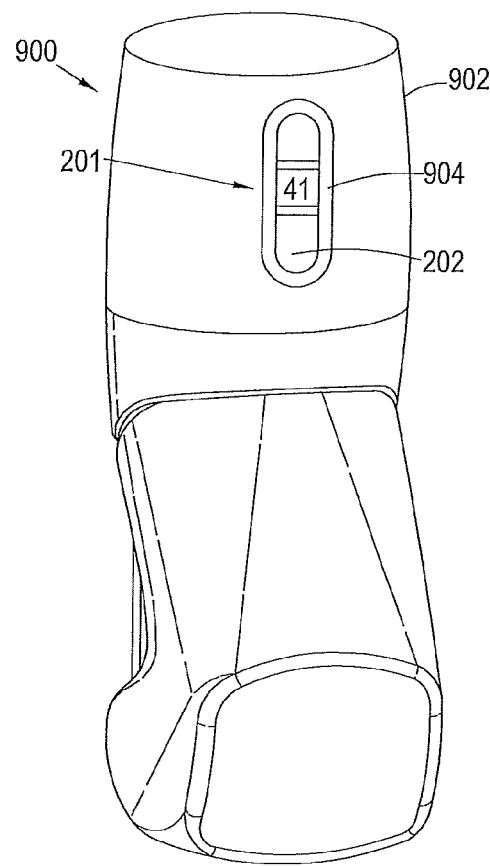
FIG. 9 is a perspective external view of the dispenser of FIG. 8.

With reference to FIG. 9, the depicted dispenser 900 has an outer housing 902 attached to or integral with the body of the dispenser. The second member 202 is superimposed under a window 904 of the outer housing. The teeth-bearing member, which is hidden from view, fixes the second member 202 positionally (here offset by approximately 90 degrees compared to its position in FIG. 8) in relation to the window. As can be readily ascertained from FIG. 9, the first member 201 and the second member 202 of the dose counter overlap such that only a portion (shown with the indicium "41") of one turn of the first member 201 is exposed to the window.

Figure 10:
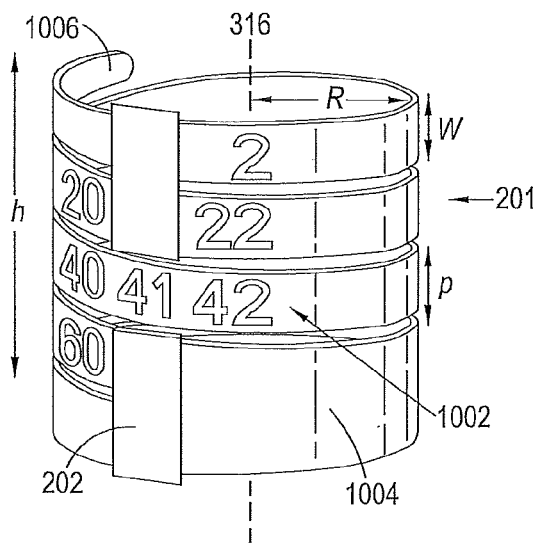
FIG. 10 is a perspective view of a counter according to one embodiment of the present invention.

An exemplary overlapping relationship is detailed in FIG. 10. The first member 201 exhibits numeric indicia 1002, and is arranged in multiple turns (three in this case) about an axis 316. In this particular example, the numbers of the set $\{0, 1, \ldots, 60\}$ decrease in integer steps of one from a base portion 1004 to a tip portion 1006 of the member, but in other arrangements the numbers may decrease from the tip portion to the base portion. A second member 202 extends over a portion of each of the turns except one, such that only a single numeric integer ('41') is displayed across its width. Numbers (and other indicia) may alternatively be oriented in other directions relative to those shown here, such as rotated by 90 degrees.

In addition to different indicia, many of the structural characteristics associated with the first member 201 may be varied, including the pitch p, the strip width W, the height h, and the radius of curvature R, depending on the shape, number of held doses and configuration of the container and dispenser. To give but one example, the first member 201 could be a triangular strip, i.e. broad at one end and tapering to the other end. Further, the material of either or both of the first and second members 201, 202 may be selected from a range of available materials such as papers and plastics.

Figure 11:
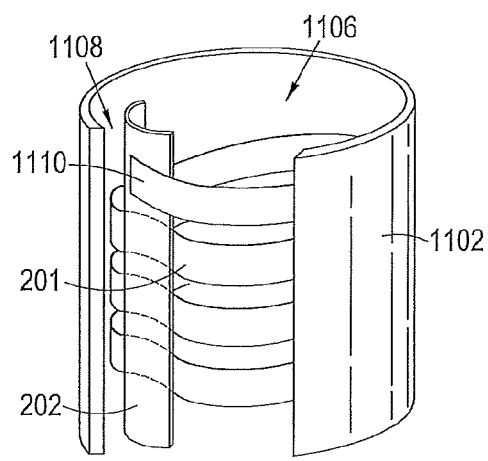
FIG. 11 is a perspective view of a counter according to another embodiment of the present invention.

In an alternative overlapping relationship of the dose counter, shown in FIG. 11, a dose counter comprising a rigid outer element 1102 and a rigid second member 202 define a recess 1106 (e.g. for a container) and a channel 1108. A first end 1110 of a flexible first member 201 is threaded into the channel between the outer element 1102 and the second member 202, gradually winding through the channel 1108 as the contents of the container are dispensed.

In FIG. 12, the first member 201 makes one complete helical turn. A suitably windowed outer housing 902 of the dispenser is superimposed over the second member 202. The window 904 is configured such that only a portion 201a of the first member is presented. The second member comprises an element within the diameter of the first member.

In an alternative arrangement the window 904 of the housing 902 can effectively function as the second member and the second member can be omitted. Thus the window 904 of the housing 902 can function to present only a portion of a single or partial helical turn of the first member.

In FIG. 13, the first member 201 comprises a triangular strip wrapped within the housing 902 and having at least an upper edge 201b making a complete helical turn, with the second member 202 being behind the first member when viewed through the window 904. As the first member is rotated, the ratio between the visible portion 202a of the second member 202 and the visible portion 201a of the first member increases. Suitable colouring, such as green for the first member and red for the second member, provides a fuel-gauge type counter. Alternatively or additionally indicia may be provided on the housing 902.

In FIG. 14, the first member 201 is provided with a guide element G for guiding first member 201. The guide element G shown in FIG. 14 comprises a track which extends along the entire length of the first member 201. In other embodiments, however, the guide element G may only extend along portions of the length of the first member 201. The guide element G helps to ensure that the first member 201 does not compress as it rotates.

While a dose counter should accurately track the number of doses released from/remaining in a medicament container, it is also desirable that a count is registered before a corresponding dose is released to the user. This reduces the possibility of user abuse. Thus, where the dispenser includes a drive mechanism and a retaining mechanism such as a kinked-valve, an irreversible count may be initiated by the first engagement, which coincides with a release of a dose into the kinked valve, and completed by the second engagement, which coincides with reset after the release from the kinked valve to the user.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A counter comprising:
 a first member disposed in at least a partial helical turn about a longitudinal axis of an entity whose movements and/or contents are to be counted, said first member having an indicium or indicia indicative of a count;
 a second member extending generally in the direction of said longitudinal axis, said second member being operatively disposed in overlapping relationship under and over one or more portions of said at least partial helical turn of said first member, when viewed from the outside; and means to effect relative movement between said first and second members, said movement comprising a relative incremental rotation about said longitudinal axis.

2. A counter as claimed in claim 1, wherein said entity is a medicament container for a dispenser having a body for receiving said medicament container and a dispensing mechanism for dispensing a dose of medicament from said medicament container.

3. A counter as claimed in claim 2, wherein said movement is performed in a relative incremental rotation in response to said dispenser being actuated.

4. A counter as claimed in claim 2, wherein said indicium or indicia is or are indicative of the number of doses of medicament dispensed from, or remaining in, said container.

5. A counter as claimed in claim 2, wherein said first member helically disposed about a longitudinal axis of said dispenser body has a substantially constant pitch and/or width along its length.

6. A counter as claimed in claim 2, wherein said first member helically disposed about a longitudinal axis of said dispenser body has a varied pitch and/or width comprising one or more discrete sections of different pitch and/or width along its length.

7. A counter as claimed in claim 1, wherein said means to effect a relative rotation comprises a drive mechanism having a pawl-bearing member arranged and configured to releasably engage a tooth-bearing member.

8. A counter as claimed in claim 7, wherein said drive mechanism biases said first member in a rotational direction about said longitudinal axis responsive to a force in a direction substantially parallel to said longitudinal axis.

9. A counter as claimed in claim 8, wherein a rotation of said first member from a first position to a second position is initiated prior to a dispensing of the product.

10. A counter as claimed in claim 7, wherein said first member is driven by said drive mechanism.

11. A counter as claimed in claim 2, wherein said second member is fixed relative to said dispenser.

12. A counter as claimed in claim 2, wherein said first member rotates about said longitudinal axis of said dispenser.

13. A counter as claimed in claim 2, wherein said dispenser includes a housing having a window in substantial alignment with said second member, and wherein said overlapping relationship is such that only one portion of said at least a partial helical turn of said first member is exposed to said window.

14. A counter as claimed in claim 1, wherein said first member is disposed in a plurality of helical turns about said longitudinal axis.

15. A counter as claimed in claim 1, wherein said second member extends in a direction parallel to said longitudinal axis.

16. A counter as claimed in claim 1, wherein said relative incremental rotation about said longitudinal axis changes said overlapping relationship between said first and second members.

17. A counter as claimed in claim 1, wherein said overlapping relationship is such that only a portion of one partial turn or turn of said first member lies over or under, said second member.

18. A counter as claimed in claim 17, wherein said indicium or indicia is provided on said first member to be located over or under, said second member.

19. A counter as claimed in claim 18, wherein said indicium or indicia is provided on said first member to be located over said second member.

20. A counter as claimed in claim 17, wherein said overlapping relationship is such that only a portion of one partial turn or turn of said first member lies over said second member.

21. A counter as claimed in claim 1, wherein said second member comprises a strip of flexible, resilient or rigid material.

22. A counter as claimed in claim 1, wherein said first member comprises a rigid, resilient or flexible material.

23. A counter as claimed in claim 1, wherein one or both of said first and second members is comprised of a low friction coefficient material.

24. A counter as claimed in claim 1, wherein said indicium or indicia is or are provided by a shape of the first member and/or indicia comprising one or more of: numbers, colours, letters and symbols.

25. A counter as claimed in claim 24, wherein said indicia comprise a set of numbers sequential in increments of one or more of: a fraction of one, one, two, five, ten, twenty, fifty, and a hundred.

26. A counter as claimed in claim 24, wherein said indicia are printed, cut out from, embossed, molded, adhered, incorporated, or painted on one or both of said first and second members.

27. A dispenser comprising the counter as claimed in claim 1.

28. A dispenser as claimed in claim 27 which is a pressurised metered-dose inhaler (pMDI).

29. A dispenser comprising:
a body for receiving a medicament container;
a medicament container;
a dispensing mechanism for dispensing a dose of medicament from said container; and
a counter as claimed in claim 1.

30. A dose counter for use with a dispenser having a body for receiving a medicament container and a dispensing mechanism for dispensing a dose of medicament from said container, the dose counter comprising:
a first member disposed in at least a partial helical turn about a longitudinal axis of said medicament container and having an indicium or indicia indicative of the number of doses of medicament dispensed from, or remaining, in said container;
a second member extending generally in the direction of said longitudinal axis, said second member being operatively disposed in overlapping relationship under and over one or more portions of said at least partial helical turns of said first member, when viewed from the outside; and
means to effect relative movement between said first and second members when said dispensing mechanism is actuated, said movement comprising a relative incremental rotation about said longitudinal axis.

31. A dose counter for use with a dispenser having a body for receiving a medicament container and a dispensing mechanism for dispensing a dose of medicament from said container, the dose counter comprising:
a first member disposed in a single or partial helical turn about a longitudinal axis of said medicament container and having an indicium or indicia indicative of the number of doses of medicament dispensed from, or remaining, in said container;
a second member extending generally in the direction of said longitudinal axis, said second member being operatively disposed in overlapping relationship under and over one or more portions of said at least partial helical turn of said first member, when viewed from the outside;

a housing having a window extending generally in the direction of said longitudinal axis, said housing being operatively disposed in overlapping relationship with said first member such that only one portion of said single or partial helical turn of said first member is exposed to said window; and means to effect relative movement between said first member, and said second member and said housing when said dispensing mechanism is actuated, said movement comprising a relative incremental rotation about said longitudinal axis.

* * * * *